United States Patent [19]
Mitra

[11] Patent Number: 6,112,602
[45] Date of Patent: *Sep. 5, 2000

[54] ANALYTICAL APPARATUS AND INSTRUMENTATION FOR ON-LINE MEASUREMENT OF VOLATILE ORGANIC COMPOUNDS IN FLUIDS

[75] Inventor: Somenath Mitra, Bridgewater, N.J.

[73] Assignee: New Jersey Institute of Technology, Newark, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/940,641

[22] Filed: Sep. 30, 1997

Related U.S. Application Data

[63] Continuation-in-part of application No. 08/475,701, Jun. 7, 1995, abandoned, which is a continuation-in-part of application No. 07/076,414, Jun. 14, 1993, Pat. No. 5,435,169.

[51] Int. Cl.$^7$ ...................................................... G01N 1/00

[52] U.S. Cl. .......................................................... 73/863.12

[58] Field of Search ................................ 73/23.41, 23.42, 73/863.01, 863.12, 863.21, 863.71, 864.81; 422/88–91

Primary Examiner—Robert Raevis
Attorney, Agent, or Firm—Klauber & Jackson

[57] ABSTRACT

A device and method for the continuous on-line or discrete off-line concentration and measurement of organic compound contaminants in a fluid sample stream is disclosed, in which an adsorbent trap means, which may be a tube of metal packed with an adsorbent composition such as a carbon-based composition, is used to adsorb the organic compound contaminants, while venting out permanent gases, such as CO, $CO_2$, $N_2$, $O_2$, $NO_2$, $SO_2$, $CH_4$, and $H_2O$. The adsorbent trap means is capable of rapid heating and cooling, and when a pulse of electrical energy or microwave energy is applied thereto, the adsorbed organic compound contaminants are rapidly desorbed therefrom; after which they are carried to a detector means for measuring the organic compound contaminants. Embodiments are included in which gas chromatography (GC) is not employed. A sampling valve may also be used to cause the sample stream to enter and be retained in a sample retention element of the sampling valve, after which the valve may be repositioned to cause the measured portion of the sample stream to be ejected from the sample retention element and be carried to the adsorbent trap means. A computer may also be used together with a power supply and a recording device in order to control all of the operations and measurements of the device and method, so that they are carried out in accordance with a predetermined schedule, or in response to the dictates of said sample measurements, or both.

8 Claims, 13 Drawing Sheets

1. $CO_2$, CO and $CH_4$
2. NMOC

1. $CO_2$, CO and $CH_4$
2. NMOC

1. Benzene
2. Hexane
3. Toluene
4. Tetra-cl-ethylene
5. Cl-benzene
6. Ethyl-benzene

ANALYTICAL APPARATUS AND INSTRUMENTATION FOR ON-LINE MEASUREMENT OF VOLATILE ORGANIC COMPOUNDS IN FLUIDS

CROSS REFERENCE TO RELATED APPLICATION

This application is a continuation-in-part of application Ser. No. 08/475,701, filed Jun. 7, 1995, now abandoned; which is a continuation-in-part of application Ser. No. 07/076,414 filed on Jun. 14, 1993, and now U.S. Pat. No. 5,435,169.

FIELD OF THE INVENTION

The present invention relates to methods and devices for continuous on-line and discrete off-line monitoring of organic compound contaminants in fluid streams. The present invention is particularly concerned with monitoring concentrations of such contaminants in terms of recognized categories based on different analytical techniques: total organic carbon (TOC), non-methane organic carbon (NMOC), and volatile organic compounds (VOCs). The fluid streams in which such organic compound contaminants can be found, and in which their presence must be detected and their concentrations measured, are, e.g., those fluid streams emitted from industrial and commercial stacks, those discharged as effluents from air toxic control devices and as waste water from plants, and those present in drinking water sources.

BACKGROUND OF THE INVENTION

Organic compound contaminants, especially volatile and volatilizable organic compounds (VOCs) in the environment may be hazardous to public health even at very low concentrations, since many of the VOCs are toxic, mutagenic, and/or carcinogenic, such as aromatic and halogenated compounds. Organic compound contaminants which are "volatile", as that term is used in the present invention, are those which have a relatively high vapor pressure and can be found in vapor form at relatively low temperatures. However, there is also included within the definition of "volatile organic compounds" (VOCs), as that term is used in the present invention, organic compounds which are "volatilizable", i.e., capable of being made volatile. Such volatilizable organic compounds are particularly those which may vaporize under the conditions of concentration and detection to be found during the methods of the present invention. The measurement of VOCs in air has become a very important goal. Conventional VOCs monitoring methods involve collecting a sample at the site and transporting it to the laboratory for analysis. While these methods are quite accurate, they cannot be utilized for continuous on-line analysis to provide information on a real-time basis as required for effective pollution control and for meeting regulatory requirements. A discussion of such methods, and of the state of the art relating to them, can be found in U.S. Pat. No. 5,435,169, which is incorporated herein by reference in its entirety.

In accordance with the present invention, analytical apparatus and instrumentation is provided which can be used in various aspects of continuous on-line measurement of organic compound contaminants, and which can also be used off-line for isolated, i.e., discrete measurements which may be single instances or repetitive occurrences. The objective of the analytical apparatus and instrumentation is three-fold. The organic compound contaminants are to be concentrated to facilitate detection of low concentrations; interfering species such as $CO_2$ and $H_2O$ are to be eliminated; and then the trapped organic compound contaminants are to be injected into the detector. A variety of detector systems may be used with this analytical approach, e.g., non-methane organic carbon analysis (NMOC), total organic carbon analysis (TOC), mass spectrometry (MS), infrared spectroscopy (FIR), or any other suitable detection system. Systems of this type can be used on-line to monitor emissions from industrial stacks, vents and similar sites from which emissions originate.

Total Organic and Non-Methane Organic Carbon Analysis—Total organic carbon is a measure of total carbon emissions in organic form, i.e., the total carbon content less that derived from the permanent gases such as $CO_2$ and CO. Non-methane organic carbon (NMOC) is another category of organic compound contaminant measurement frequently used in addition to total organic carbon, and is a measure of the total organic carbon content of a sample, except that coming from methane. In non-methane organic carbon analysis, methane, $CH_4$, is treated as a permanent gas, although it is not treated as a permanent gas in the other analyses.

In the mid-1970's, EPA Standard Method 25 was developed for quantifying NMOC emissions from stationary sources. In that method, gas samples are collected and sent to a lab for analysis. In a conventional non-methane organic carbon analyzer, one milliliter of gas sample is introduced into a separation column a through a gas sampling valve. The column is used to separate VOCs from permanent gases such as $CO_2$, $CH_4$ and CO. After the gases elute from the column, i.e., a $CO_2$ peak appears, the column is backflushed into the detector system and all of the organics are then measured together as one peak.

The detection system comprises an oxidation unit, a reduction unit and a flame ionization detector (FID). The reason for converting all of the organic compounds to $CH_4$ is that different compounds have different response factors in FID, and in this manner a response directly proportional to the number of carbon atoms is obtained.

The use of column separation in conventional NMOC analysis poses significant problems especially when the sample contains large amounts of moisture and the concentration of $CO_2$ is above 8% by volume of the sample. Another major problem is that the detection limits are not low enough, as a result of the fact that the injection volume must be limited in order to obtain good separation in the column. Another drawback of this method is that it cannot be used for continuous on-line monitoring. Other total organic carbon analysis methods are also used where, instead of reducing the $CO_2$ to methane, the $CO_2$ itself is measured using infrared or other suitable detection means.

Continuous On-Line FID, MS and FTIR—At present on-line analysis is done using a flame ionization detector (FID) for total hydrocarbon analysis. Similarly, the mass spectrometer (MS) and the Fourier Transform. Infrared Spectrophotometer (FTIR) are used for on-line VOCs monitoring. In the case of both the FID and the MS, the sample is introduced directly into the detector. No sample concentration is used, and thus the detection limits are quite high. However, $H_2O$, CO and $CQ_2$, which are always present in environmental emissions, interfere in the analysis. In the case of the FTIR, the absorbance spectra is measured in a flow cell, or else a long path FTIR is used in which the IR beam is reflected across the emission source. Here also, the presence of $H_2O$, CO and $CO_2$ can also interfere with the analysis.

Monitoring VOCs in Water—Most conventional VOCs monitoring is done by using the purge and trap method. Typically, the sample is collected in the field and then transported to the laboratory. On-line purge and trap systems have also been developed for semi-continuous monitoring.

SUMMARY OF THE INVENTION

In accordance with the present invention, devices and methods are disclosed for the continuous, substantially real-time, monitoring of very low level concentrations, i.e., levels below parts per million by volume (ppm), and even levels below parts per billion by volume (ppb), of organic compound contaminants for environmental and chemical process, monitoring and control purposes. The device has general utility in effectively continuous on-line monitoring using different detection devices such as those for non-methane organic carbon (NMOC) and total organic carbon (TOC); specific devices, e.g., the mass spectrometer (MS) and the Fournier Transform Infrared Spectrophotometer (FTIR); total hydrocarbon analysis using a Flame Ionization Detector (FID), Gas Chromatograph (GC) associated detectors; and other detector means, e.g., the Electrolytic Conductivity Detector (ELCD), Electron Capture Detector (ECD), Thermionic Ionization Detector (TID), Nitrogen Phosphorous Detector (NPD), Flame Photometric Detector (FPD), and Thermal Conductivity Detector (TCD), and so forth.

The key operating feature of the method of the present invention is the use of an adsorbent trap means for the organic compound contaminants, which may be based, e.g., on the differential adsorbent capacity of compositions such as activated carbon, on the differential temperature effects of cryogenic processes, etc., to capture and retain the organic compound contaminants while the interfering and background species, e.g., $H_2O$, $CO_2$, CO, etc., are permitted to pass through. The organic compound contaminants are then released quickly from the adsorbent trap means, preferably through a rapid desorption achieved by the heating of the adsorbent trap means. Following desorption, the sample is injected into one of the detector means identified above, e.g., by the use of an inert carrier gas.

The devices and methods of the present invention are useful for the detection and measurement of organic compound contaminants in fluid sample streams. The fluid stream may be either gaseous, e.g., air, or liquid, e.g., water. Where the sample stream is gaseous, it is preferred that the detector means be other than gas chromatography (GC). Gas chromatography is, properly, a means for separating the components of a sample, and a detector means associated therewith may be used to "read" the results, i.e., to physically identify the separated components. It has been found that by using the adsorbent trap means of the present invention and rapid desorption of the organic compound contaminants therefrom, that it is not necessary to employ gas chromatography separation, as required in the methods of the prior art. A gas chromatographic separation step may be included, however, and is preferred in the methods of the present invention where the fluid sample stream is water or a liquid effluent containing or suspected of containing organic compound contaminants.

In U.S. Pat. No. 5,435,169, the disclosure of which is incorporated herein by reference in its entirety, a method and corresponding apparatus for the continuous, on-line GC analysis of VOCs is disclosed, which involves the collection of VOCs in a concentrator element, and the separation of the VOCs from the permanent gases, followed by the introduction of the sample to a gas chromatography (GC) column. The concentrator element is an adsorbent trap means containing at least one adsorbent that is able to separate the organics by adsorption, while venting the permanent gases. The concentrator is purged by desorption and the desorbed gases are then injected into the GC and associated detector. This process is performed rapidly and frequently in order to achieve effectively continuous on-line monitoring. This process and the corresponding apparatus are outlined in U.S. Pat. No. 5,435,169 with respect to VOCs and the injection of the concentrated material into a GC. However, the need for greater analytic simplicity, together with extended functioning of the adsorbent trap means for separation of a more specific array of interfering materials, has led to its implementation with additional detector means such as FID, MS, FTIR, ELCD, ECD, TID, NPD, FPD, and TCD, and additional applications such as the monitoring of NMOC and TOC concentrations. The resulting improved method and corresponding apparatus for continuous on-line use of the present invention will now be described.

Application in NMOC, FID, MS and FTIR Monitoring— The method of the present invention is quite different from the conventional on-line NMOC, TOC, FID, MS or FTIR analysis. The sample containing the organic compound contaminants is passed directly through an adsorbent trap, which selectively retains the volatile organics while allowing the other gases, e.g., CO, $CO_2$, $O_2$, $N_2$, $SO_2$, and $NO_2$, as well as moisture, to pass through. Then the trap is rapidly heated by electrical, microwave or other heating sources to desorb the organic compound contaminants into the detection system. The adsorbent trap is designed to heat and cool very rapidly, so that injections can be made very frequently, e.g., every few seconds to every few minutes. Substantially continuous analysis is possible by repeating this cycle frequently. The trap serves three purposes: (1) trapping and concentrating the organic compound contaminants; (2) separating moisture and the permanent and other gases from the sample; and (3) injecting the organic compound contaminants into the detector instrument. Measurements at very low concentration levels are possible because the pollutants are concentrated within the trap, which can be used by itself or in conjunction with other injection devices, especially a conventional sample valve.

Monitoring Organic Compound Contaminants in Water— The method and device of the present invention can also be used for the monitoring of organic compound contaminants in water. The aqueous sample containing the organic compound contaminants passes through a membrane module in which the organic compound contaminants selectively migrate across the membrane into an inert gas stream. The organic compound contaminants are trapped and concentrated by an adsorbent trap means. The retained organic compound contaminants are desorbed from the adsorbent trap means by an electrically generated heat pulse which also serves as an injection for GC separation. As an alternative to membrane separation, the separation can be accomplished by sparging. The subsequent analysis can be done by any detection system, e.g., FID, TOC, MS, FTIR, or GC.

More specifically, the present invention comprises a method for the continuous or discrete monitoring of concentrations at trace levels as low as fractional parts per billion, of TOC/NMOC as well as VOCs, pollutant levels in a fluid stream. The method comprises the steps of collecting at least one sample of the organic compound contaminants using collecting means, from the fluid stream and concentrating said collected samples using concentration means. At predetermined time periods, the concentrated, collected samples are desorbed from the concentration means, using desorption means; and the desorbed, concentrated, collected samples are injected into a detector. The steps are repeated rapidly on a regular and continuing basis in order to provide substantially real time, effectively continuous on-line monitoring. Detectors specifically include FTIR, TOC/NMOC analyzers, GC detectors, e.g., FID, NPD, FPD, TID, TCD, and ECD, mass spectrometers (MS), as well as any sensor in general. In the case of water, the organic compound contaminants are first separated, e.g., by membrane separation or sparging, after which the analysis may be done by any of the above-mentioned detectors or GC-associated detectors.

These and other objects, features and advantages of the present invention will become more evident from the following discussion and drawings.

DETAILED DESCRIPTION OF THE INVENTION

Figure 1:
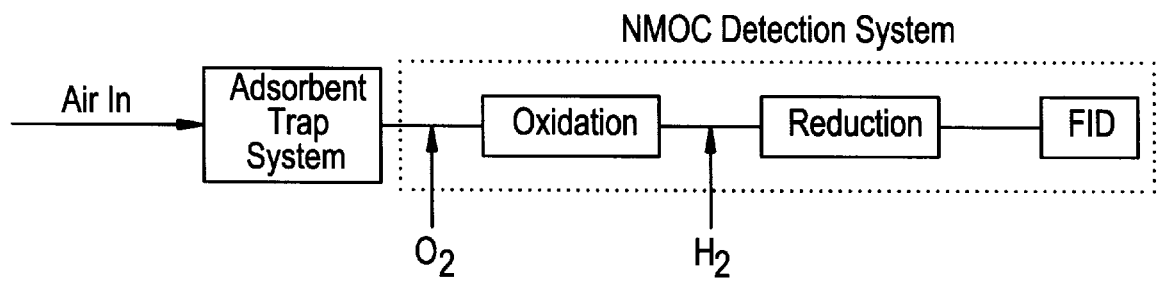
FIG. 1 is a schematic diagram of the NMOC monitoring system of the present invention.
Figure 2:
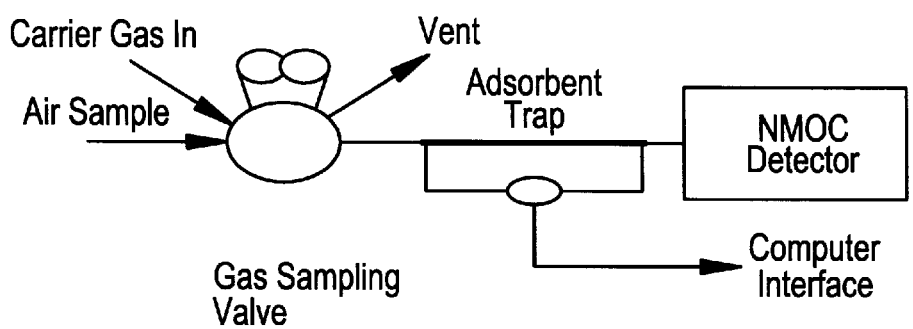
FIG. 2 is a schematic depiction of injection in the sequential valve mode (SVM) for a device of the present invention.

There will now be described in detail the analytical apparatus and instrumentation necessary to achieve the continuous monitoring of NMOC levels. This description and the principles underlying it are fully applicable to continuous monitoring using FID, MS, FTIR, and other detectors. A schematic diagram of the continuous monitoring system, as applied to NMOC monitoring, is shown in FIG. 1. The preferred gas sample valve is a six-port air actuated valve with a digit interface, e.g., one from Valco Instruments Co. Inc., College Station, Tex. A small diameter adsorbent trap, sometimes referred to as the microtrap, is made, e.g., by packing a 0.5 mm i.d., 6- to 9-inch long tube with adsorbents such as Carbotrap®, a carbon based adsorbent. Any known adsorbent having the desired affinity for organic molecules will be suitable for use with the devices and methods of the present invention. Examples of different classes of suitable adsorbents are the carbon based adsorbents, including activated carbons such as activated charcoal; molecular sieves; and the polymer-based adsorbents, including Tenax®. Various combinations of two or more of these adsorbent materials may also be used.

The adsorbent trap means is sometimes referred to herein as the on-line adsorbent trap means, or OLAT. The adsorbent trap means is connected to a variable power supply, and can be desorbed using an electrical pulse of short duration. The electrical pulse is used to cause heating of the adsorbent trap means, which in turn leads to desorption of the adsorbed species. A computer-controlled electrical switch is used to regulate the intervals between pulses and the duration of each pulse. Direct resistive heating of a metal-based adsorbent trap means is a preferred embodiment of the present invention. Other heating means for achieving the desired desorption will be within the skill of the artisan to contrive, e.g., external heating means may be used, such as a heating tape wrapped about the adsorbent trap or a heating element applied in a similar fashion, or a device for subjecting the adsorbent trap means to bombardment by microwaves of sufficient strength and duration to result in heating of the adsorbent trap means and the adsorbed organic compound contaminants therein. The adsorbent trap means is configured with a sample valve so that the organic compound contaminants are first caught by the trap, while the permanent gases such as $CO_2$, CO and $H_2O$ are vented out of the trap. An inert carrier gas such as helium (He) is then used as a carrier for the desorbed organic compound contaminants, to move them from the adsorbent trap means into the detection system.

The oxidation reactor used in the NMOC detector system is, e.g., a ¼-inch stainless steel tubing packed with Chrome Alumina, about 4 inches long. This reactor is put in a furnace, e.g., one from Lindberg, Watertown, Wis. The reduction unit is, e.g., a ¼-inch o.d. quartz tube packed with 10% nickel nitrate on Chromosorb G AW 100/120 from Varian, Calif. The typical operating temperature for the oxidation unit and reduction unit are about 650° C. and about 400° C., respectively. An FID, e.g., one from Hewlett Packard is used in the study. In another embodiment of the present invention, total organic carbon (TOC) concentration can be determined by eliminating the reduction catalyst step in the NMOC process, along with the FID detector means, and substituting for the latter a suitable $CO_2$ detector means.

Figure 5:
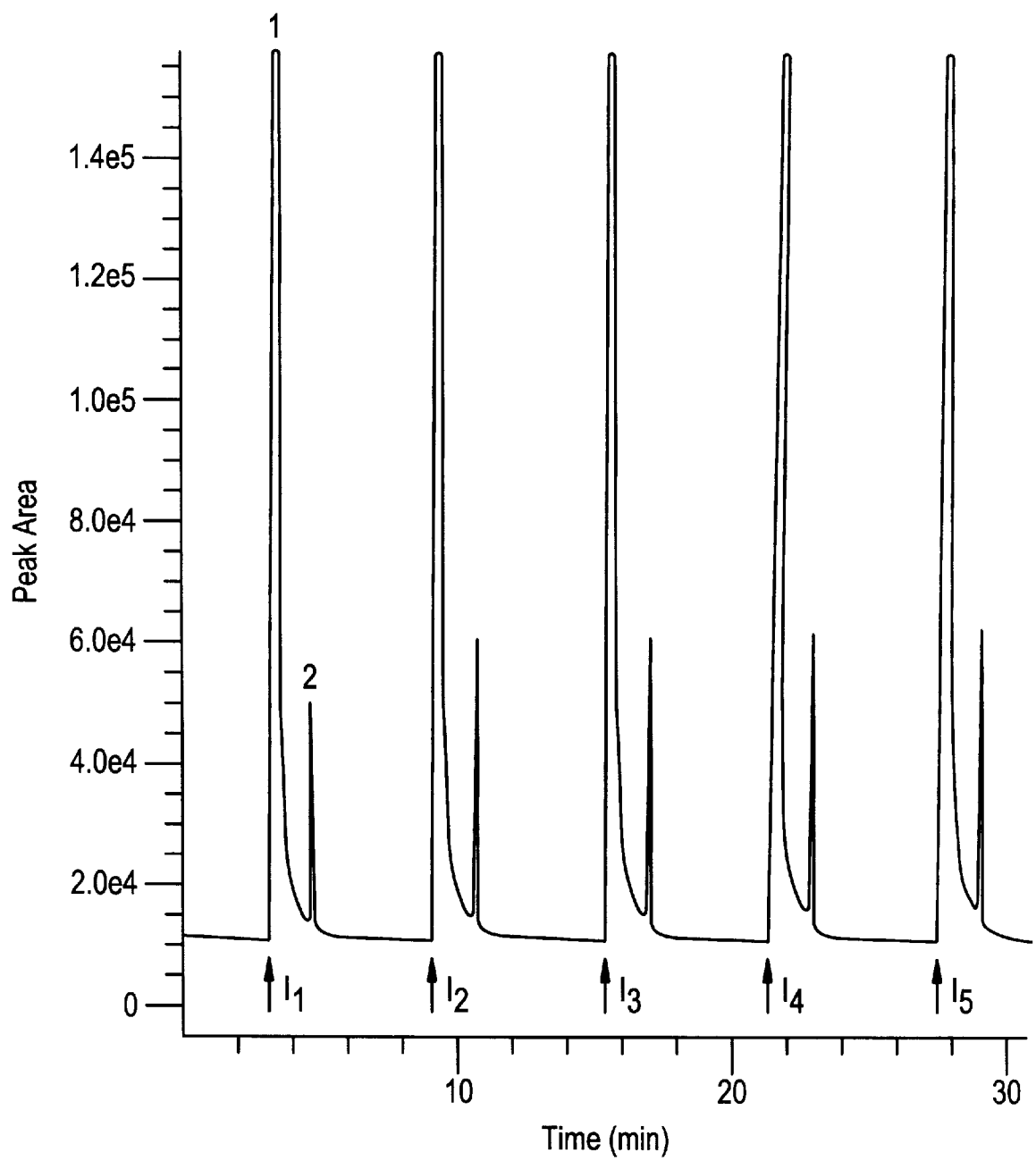
FIG. 5 illustrates the detector output obtained from the monitoring of simulated stack gas by the SVM injector and NMOC analyzer. The adsorbent trap means selectively retains organic compounds, while the permanent gases, e.g., $CO_2$, CO, $H_2O$, $O_2$, and $N_2$, pass through. First, a large peak is seen, which is due to $CO_2$, $CH_4$, and CO. Then, the adsorbent trap was desorbed by a pulse of current to obtain the NMOC peak. Adsorbent trap means pulses occurred every four minutes, at points $I_1$, $I_2$, $I_3$, etc. The flow rate of the sample stream was 6.0 ml/min. The simulated stack gas composition was as follows: benzene, 1 ppm; trichloroethylene, 1 ppm; toluene, 1 ppm; ethylbenzene, 1 ppm; oxygen, 10.9%; carbon dioxide, 9.27%; carbon monoxide, 75 ppm; sulfur dioxide 164 ppm; and the balance nitrogen.
Figure 6:
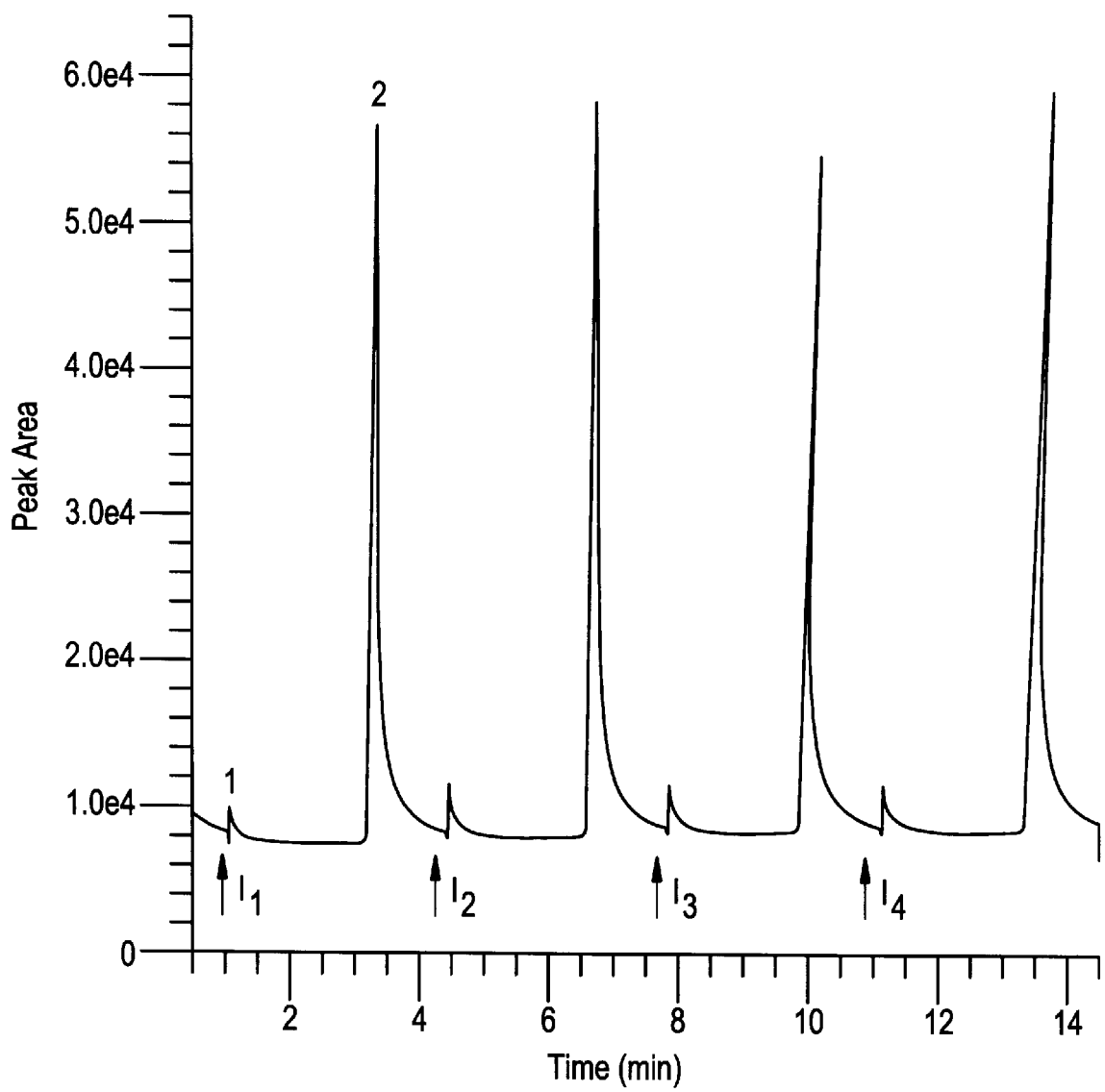
FIG. 6 illustrates a detector output obtained from the monitoring of simulated stack gas by the OLAT-BF system. First, the sample passed through the adsorbent trap means, where the organic compound contaminants were retained while the permanent gases passed through. Then, the valve was turned to the injection mode, the adsorbent trap was heated by a pulse of current in the presence of a stream of He carrier gas, and the organic compound contaminants were injected into the detector. A small peak for $CO_2$ and $CH_4$ is followed by a large peak for NMOC. The composition of the simulated stack gas was the same as in FIG. 5.

The system is operated by passing the gas to be analyzed directly through the sample injection system. Periodically, injections of sample are made by heating the adsorbent trap means, and for each desorption, a peak is seen at the instrument of the detection system. Continuous monitoring is achieved by making a series of injections at fixed intervals of from every few seconds to every few minutes, and obtaining a corresponding series of detector responses. Chromatograms illustrating such continuous monitoring are depicted in FIG. 5 and FIG. 6.

Figure 3:
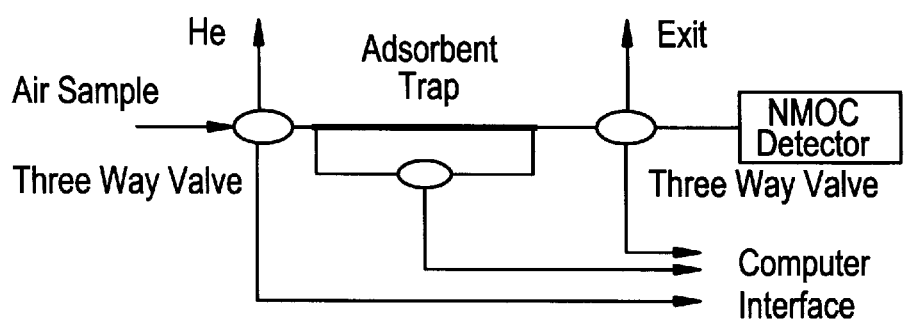
FIG. 3 is a schematic diagram of injection in the on-line adsorbent trap purge mode (OLAT-P).

The devices of the present invention can be configured in several ways, several of which are illustrated in FIGS. 1, 2, 3 and 4 The adsorbent trap means can be connected directly to the detector, as in the on-line adsorbent trap purge mode (OLAT-P) shown in FIG. 3; or as in the on-line adsorbent trap backflush mode (OLAT-BF) shown in FIG. 4. Other configurations may be used, for example that illustrated in FIG. 2, which is a sequential valve adsorbent trap means mode (SVM). In the SVM mode, one or more valve injections are made to effectively inject a large gas volume into the adsorbent trap means, which captures the organic compound contaminants. The adsorbent trap means is then heated to desorb the Organic compound contaminants into the detector. In this mode, $CO_2$, CO, $H_2O$ and other permanent and related gases, first pass through the adsorbent trap means, after which desorption of the organic compound contaminants occurs, preferably in the presence of an inert gas. In this way, these various species of gas which would otherwise interfere with the detection of the organic compound contaminants, are effectively separated from the organic compound contaminants.

Figure 4A:
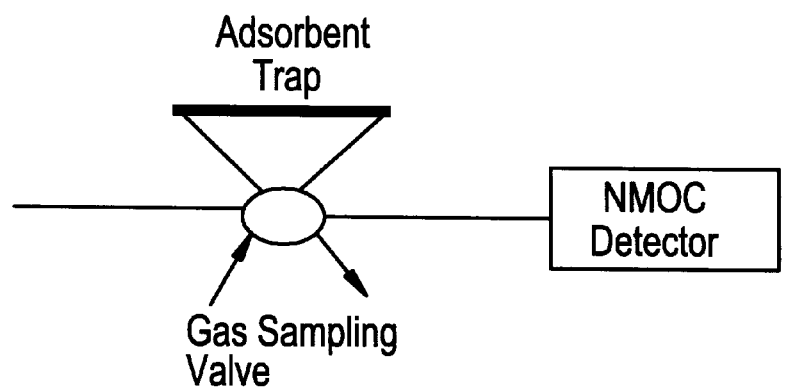
FIGS. 4A and 4B are a schematic depiction of injection in the on-line adsorbent trap back-flush mode (OLAT-BF).
Figure 4B:
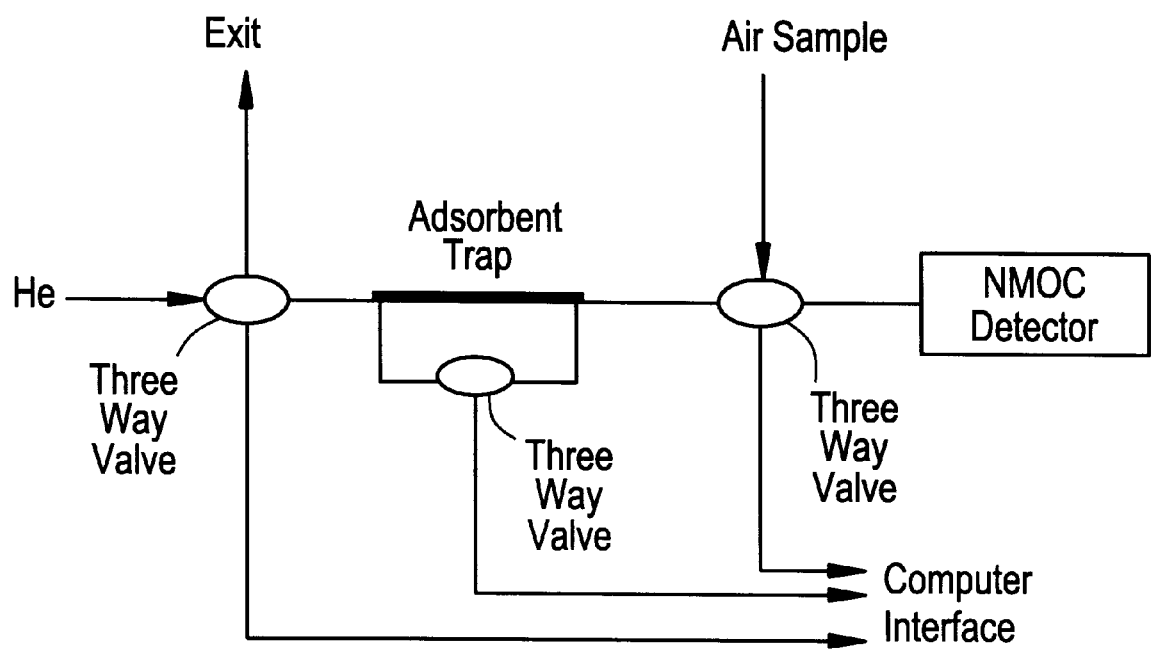

Another mode of operation of the system is to install the on-line adsorbent trap means (OLAT) with one or more valves such that the air sample passes directly through the adsorbent trap. In this mode, the analytes first pass through the trap, and $H_2O$, $CO_2$, and CO are removed. The adsorbent trap means is desorbed to inject the organic compound contaminants into the detection system. In the OLAT-P mode, two automatic three-way valves can be used, and are configured so that air sample first passes through the adsorbent trap and is vented out. Then, both valves are turned so as to be configured to pass helium, He, through the adsorbent trap; after which the adsorbent trap is desorbed and the organic compound contaminants thereby displaced are carried by the helium and injected into the appropriate detector. Other valve configurations employing, e.g., six or ten ports, may also be used, so long as they further the basic objective of the method, i.e., to eliminate the permanent gases such as CO, $CO_2$ and $H_2O$ and thereby separate them from the organic compound contaminants, and thereafter desorb the organic compound contaminants from the adsorbent trap and inject them into a detector means by way of a carrier gas such as helium. For example, it is possible to configure the system so that the adsorbent trap is backflushed into the NMOC detector, as shown in FIG. 4A. In this OLAT-BF mode a six port valve system is used. First, the sample passes through the adsorbent trap means, where the organic compound contaminants are retained while the permanent gases pass through. Then, the valve is switched, and a flow of He connects the adsorbent trap to the detector. The adsorbent trap is heated by a pulse of electrical current in order to desorb the organic compound contaminants and inject them into the detector. The desorption is carried out in the backflush mode. Backflush desorption may also be accomplished by the use of 2 three-way valves, one on either side of the absorbent trap, as shown in FIG. 4B. Using a flow direction for desorption which is the reverse of that used for sampling allows the least mobile compounds, which are separated and held in the proximate areas of the adsorbent trap, to be desorbed without being forced through the length of the trap, thus facilitating their desorption and increasing sensitivity of detection. This also becomes important with respect to the most mobile compounds, which are separated and held in the distal areas of the adsorbent trap, and are much more capable of traveling the length of the trap during desorption. These considerations play an especially important role where the adsorbent trap contains two more adsorbent materials with different adsorbent capacities, or where several different samples having different contaminants are introduced to the adsorbent trap sequentially. These situations substantially increase the likelihood that the adsorbed contaminants will be "layered", i.e., physically located in different portions of the adsorbent trap.

Figure 7:
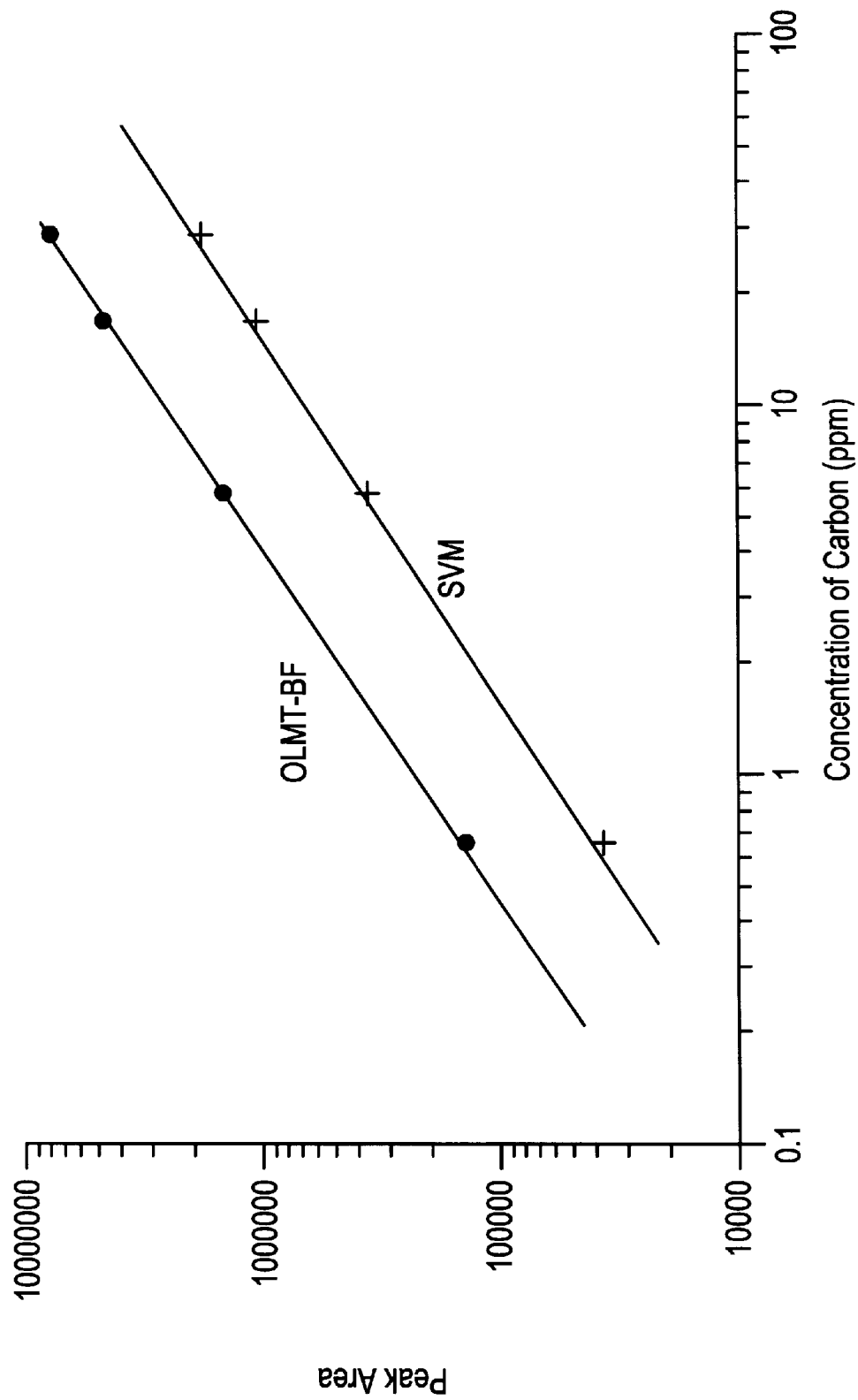
FIG. 7 is a graph showing a calibration curve for use in the NMOC system using SVM and OLAT-BF injection.
Figure 8:
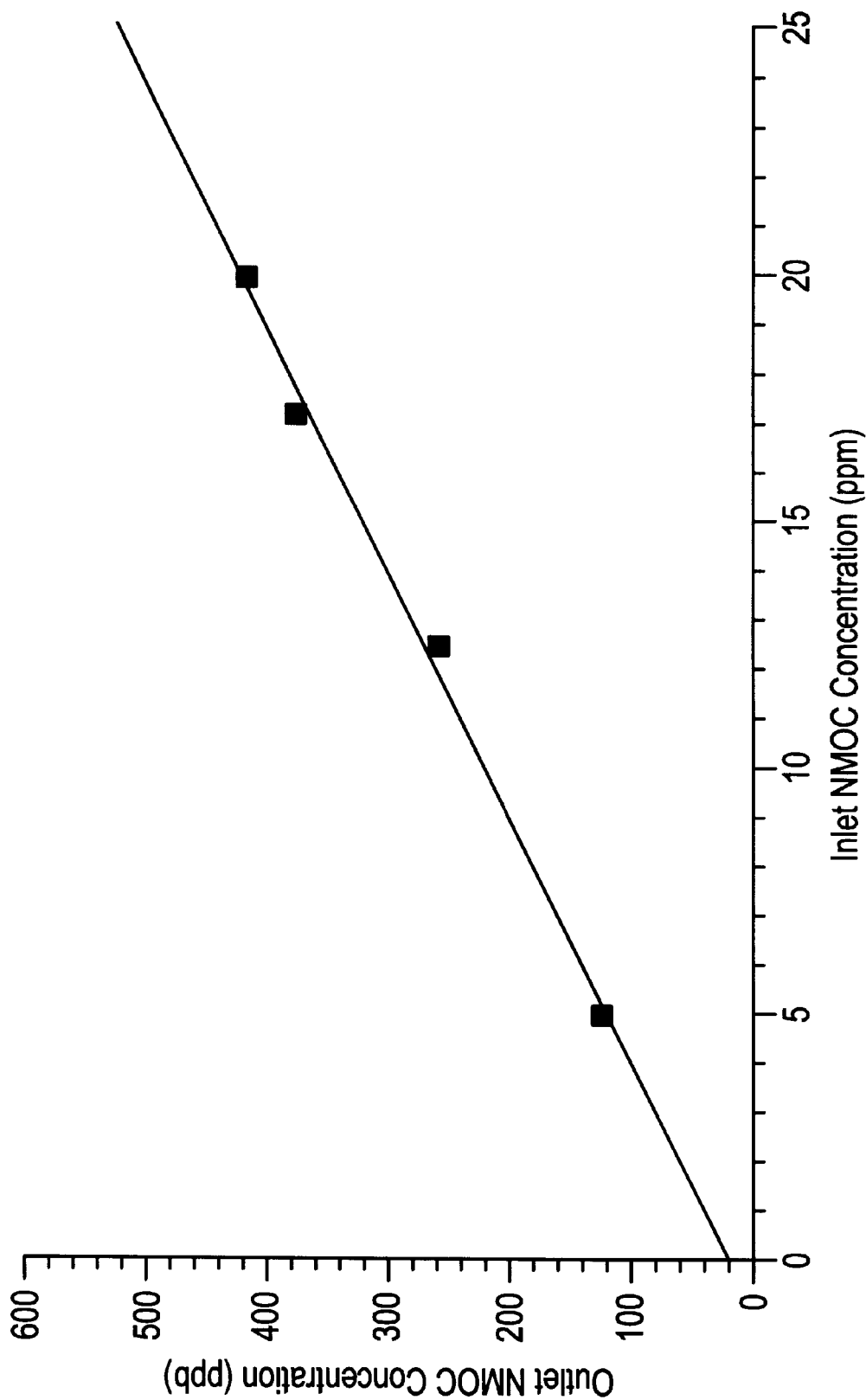
FIG. 8 is a graph showing the results from monitoring a catalytic incinerator. The inlet and outlet concentrations are plotted against each other.

Both of the modes of operation described above produce linear calibrations curves as shown in FIG. 7. A study was carried out in which the NMOC system was used to monitor the inlet and outlet of a catalytic incinerator. The results of this study are illustrated in FIG. 8, which shows that as the inlet concentration increased, the outlet concentration also increased.

Figure 9:
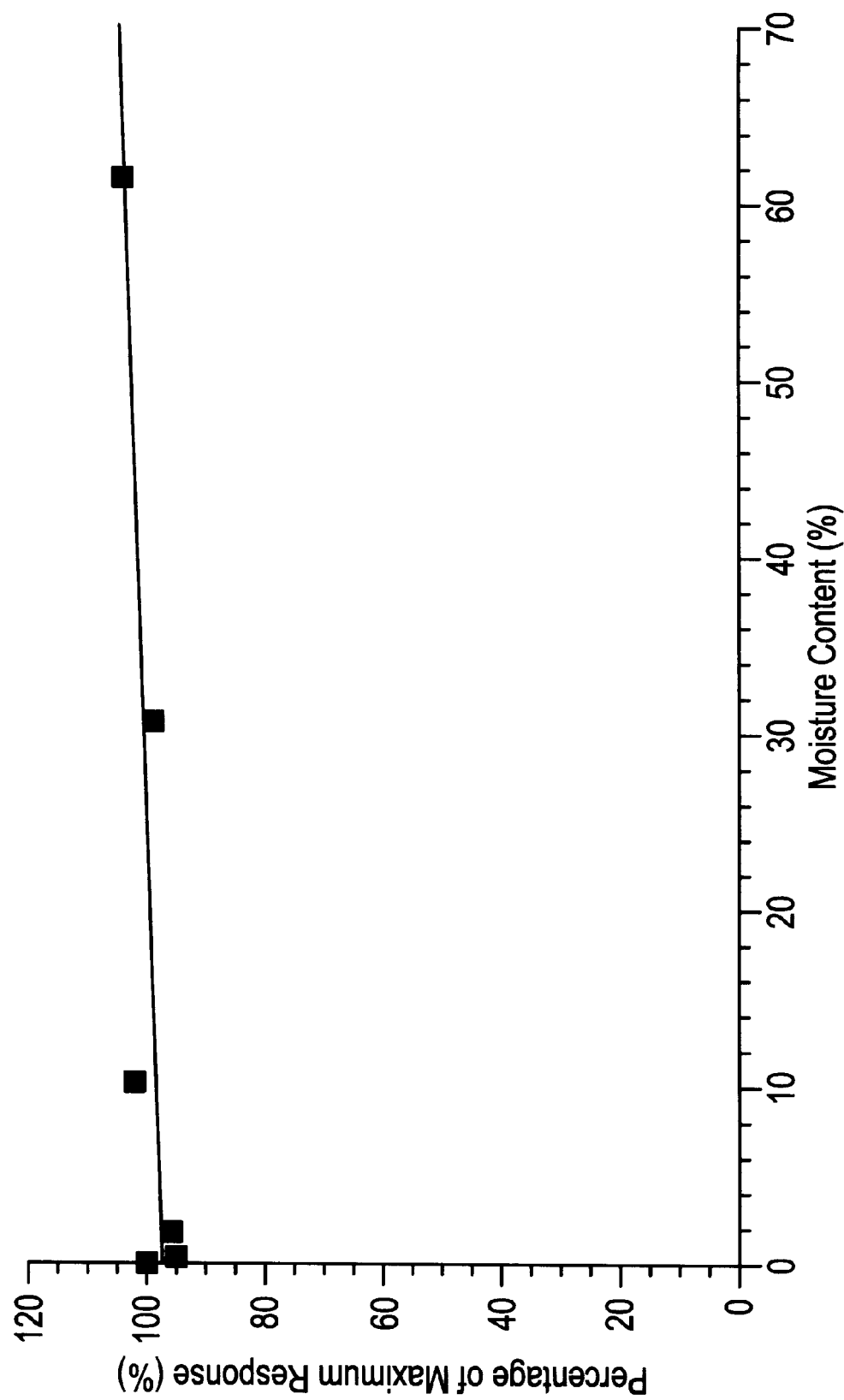
FIG. 9 is a graph showing the effect of moisture content on the NMOC system response.

A major problem with conventional NMOC analysis using EPA Method 25 is that in the presence of moisture, column separation is difficult. In the analytical apparatus and instrumentation utilized in the present invention, the adsorbents which are utilized are made of hydrophobic materials which do not retain moisture, but do capture the organic compound contaminants. Thus, the moisture is eliminated from the system and does not create problems in detection of the organic compound contaminants. As illustrated in FIG. 9, the instrument response is not affected by even large amounts of moisture. The same type of sampling system can be used in other applications. For example, the reduction unit in the NMOC system can be eliminated and a $CO_2$ detector means can be used to replace the FID detector means.

Figure 10:
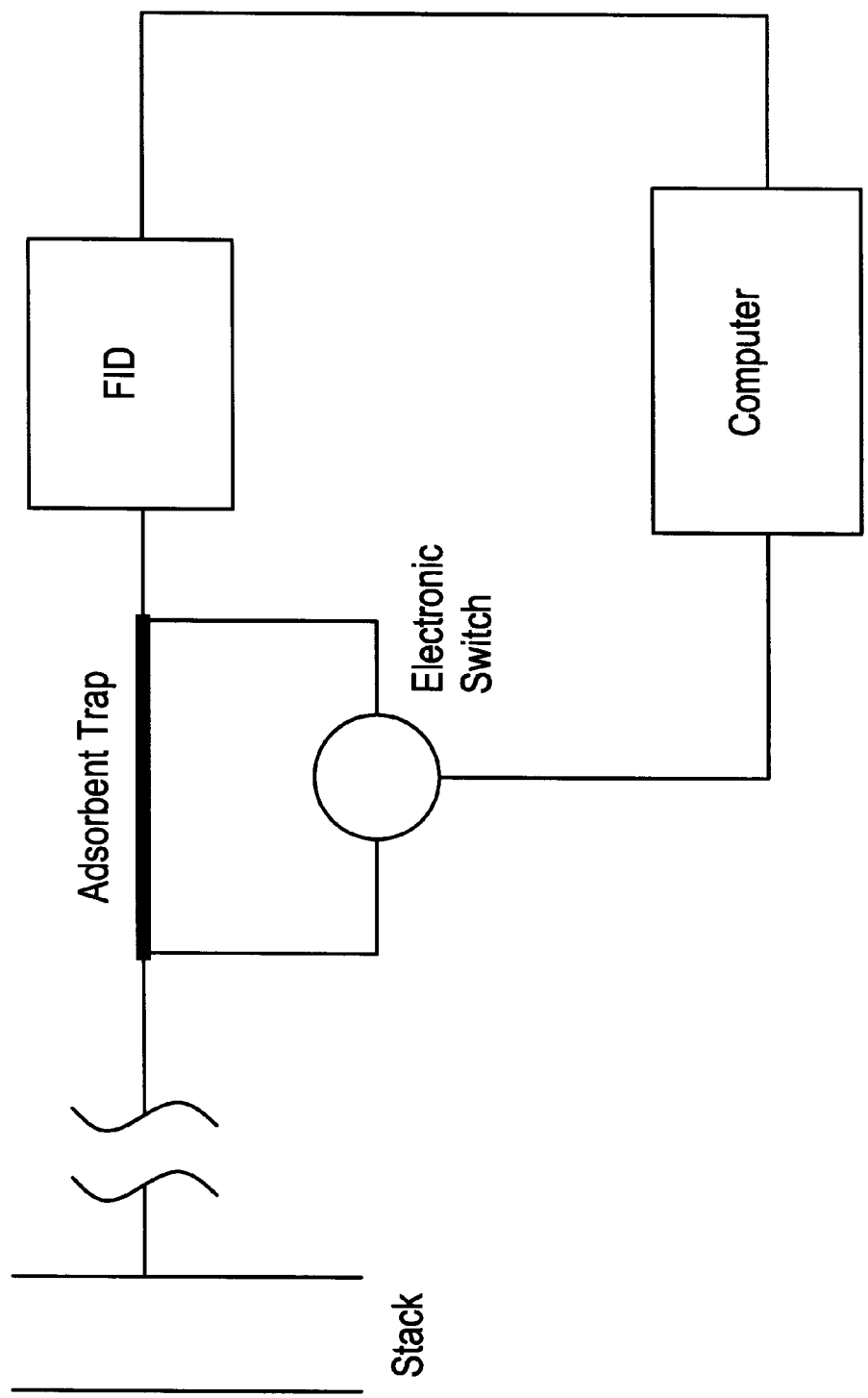
FIG. 10 is a schematic diagram for on-line monitoring of organic compound contaminants using a FID.
Figure 11:
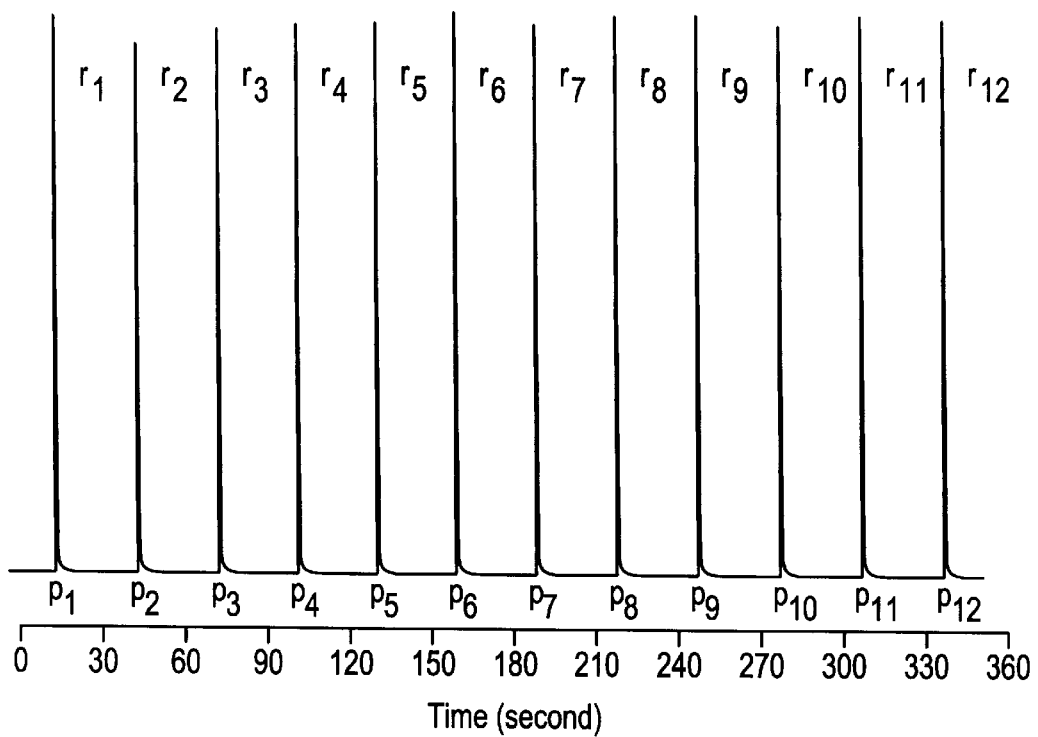
FIG. 11 is a graph showing the response of the FID using the adsorbent trap means to alternately trap and desorb organic compound contaminants as a concentration pulse.
Figure 12:
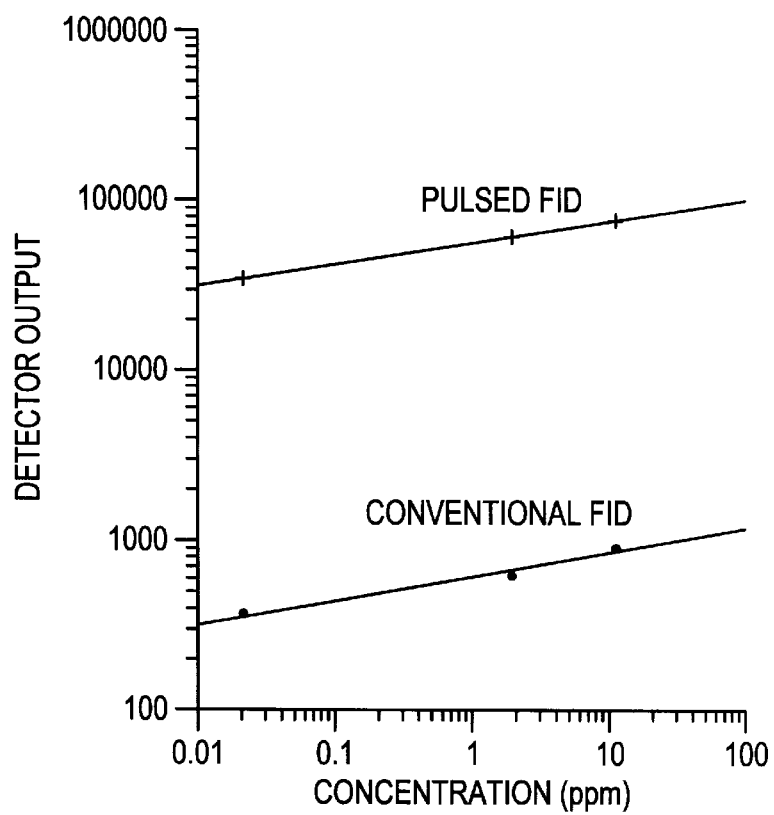
FIG. 12 is a graph comparing the calibration curves for the FID detector with and without the adsorbent trap means pulses.

Applications Utilizing FID and MS—The above-described operational modes such as SVM, OLAT-P, and OLAT-BF, can also be used in on-line FID or MS analysis. For example, as illustrated in FIG. 10, the adsorbent trap means is directly connected to the FID means. As was the case with NMOC, it has been found that a series of peaks are obtained which correspond to a series of thermal pulses transmitted to the adsorbent trap means, and this advantage of the device is clearly shown in FIG. 11, as well as in FIG. 12, where calibration curves for on-line monitoring with and without the adsorbent trap means are illustrated. From this data it can be clearly seen that the detector response utilizing the adsorbent trap means is much higher than the response without the adsorbent trap means, and that the slope of the calibration curve is also higher. Any of the configurations illustrated in FIGS. 2–4 can also be used.

Figure 13:
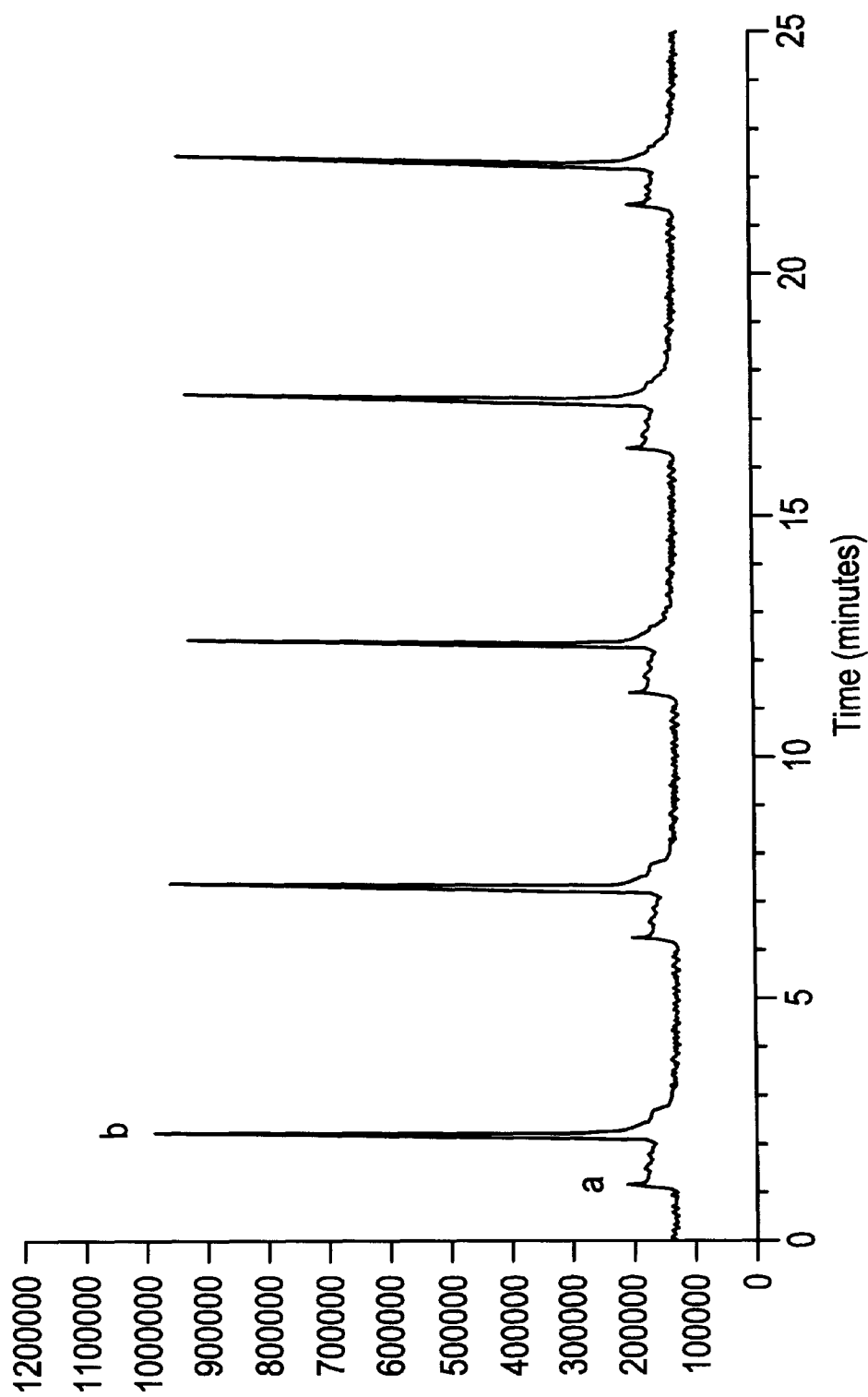
FIG. 13 illustrates continuous on-line mass spectrometric analysis of a sample stream containing toluene, in the presence of large quantities of $CO_2$ and $H_2O$.
Figure 14:
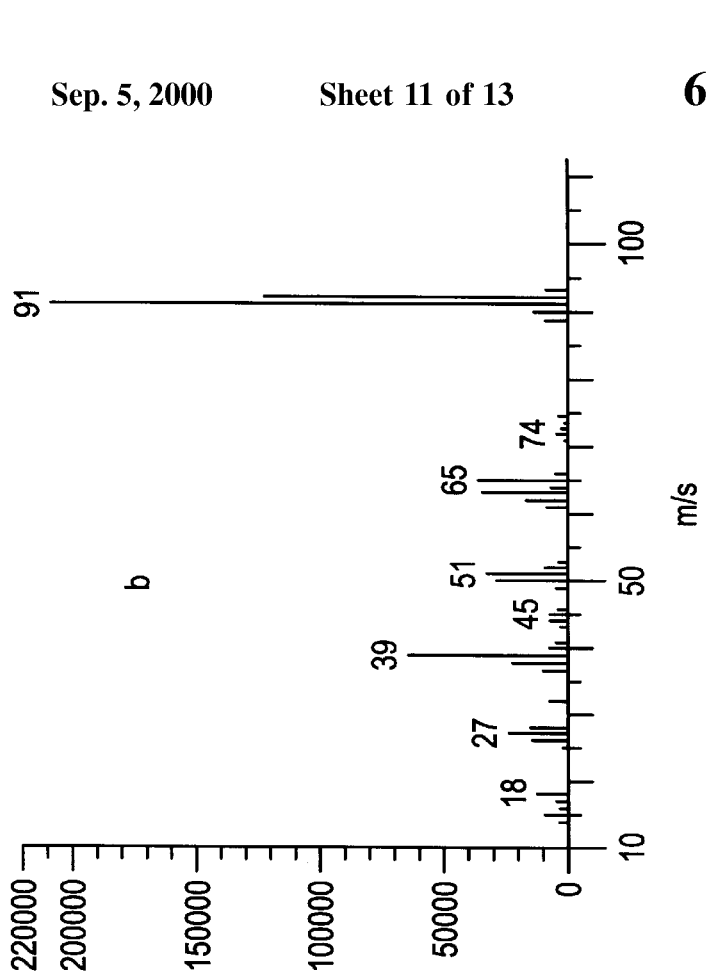
FIG. 14 is the mass spectrum of point "a" in FIG. 13, showing mainly permanent gases such as $H_2O$, $N_2$, and $CO_2$.

The above-described sampling system can also be utilized with a MS detector, and the adsorbent trap means performs in the same manner the functions of sample concentration, the elimination of interfering gas species, and the injection of the organic compound contaminants into the detector instrument. The MS generated response is illustrated in FIG. 13. One of the problems encountered with conventional on-line mass spectrometry is that $H_2O$, $CO_2$, CO, etc. present in the emission gases interfere in the ionization process. The adsorbent trap arrangements shown in FIGS. 1–4 can be used to eliminate these potentially interfering gases. The advantage of this system of the present invention in monitoring by MS is illustrated in FIG. 13. The experiment whose results are shown in the graph of this figure, was done with ppb level toluene in the presence of large quantities of $CO_2$, $H_2O$, etc. At point B, where the peak corresponding to injection from the adsorbent trap is seen, a large peak for mass 91 (toluene) is readily observable. At point A, only background gases are present. When the same sample of toluene at the same concentration was introduced directly into the MS detector means, toluene could not even be detected in the presence of such large quantities of permanent gases. It can be seen that the intensity of peaks using the adsorbent trap means based injector are much higher. The ratio of organic compound contaminants to $CO_2$ is also much higher when the adsorbent trap means based injector is used, demonstrating that the adsorbent trap means injector was able to successfully remove the $CO_2$.

Figure 15:
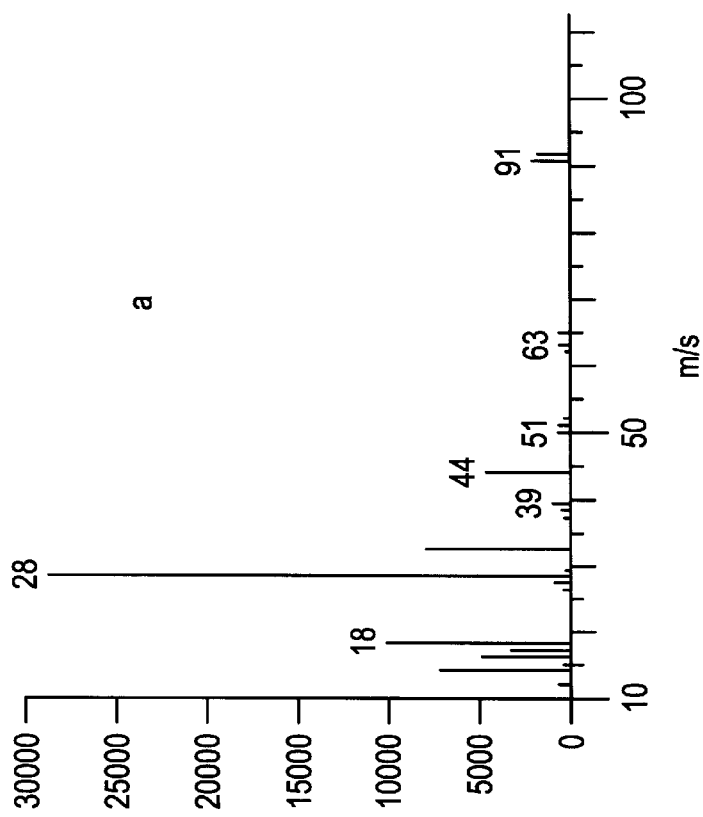
FIG. 15 is the mass spectrum at point "b" in FIG. 13, showing the results of desorption of the adsorbent trap means, where toluene, mass 91, is the main product.
Figure 16:
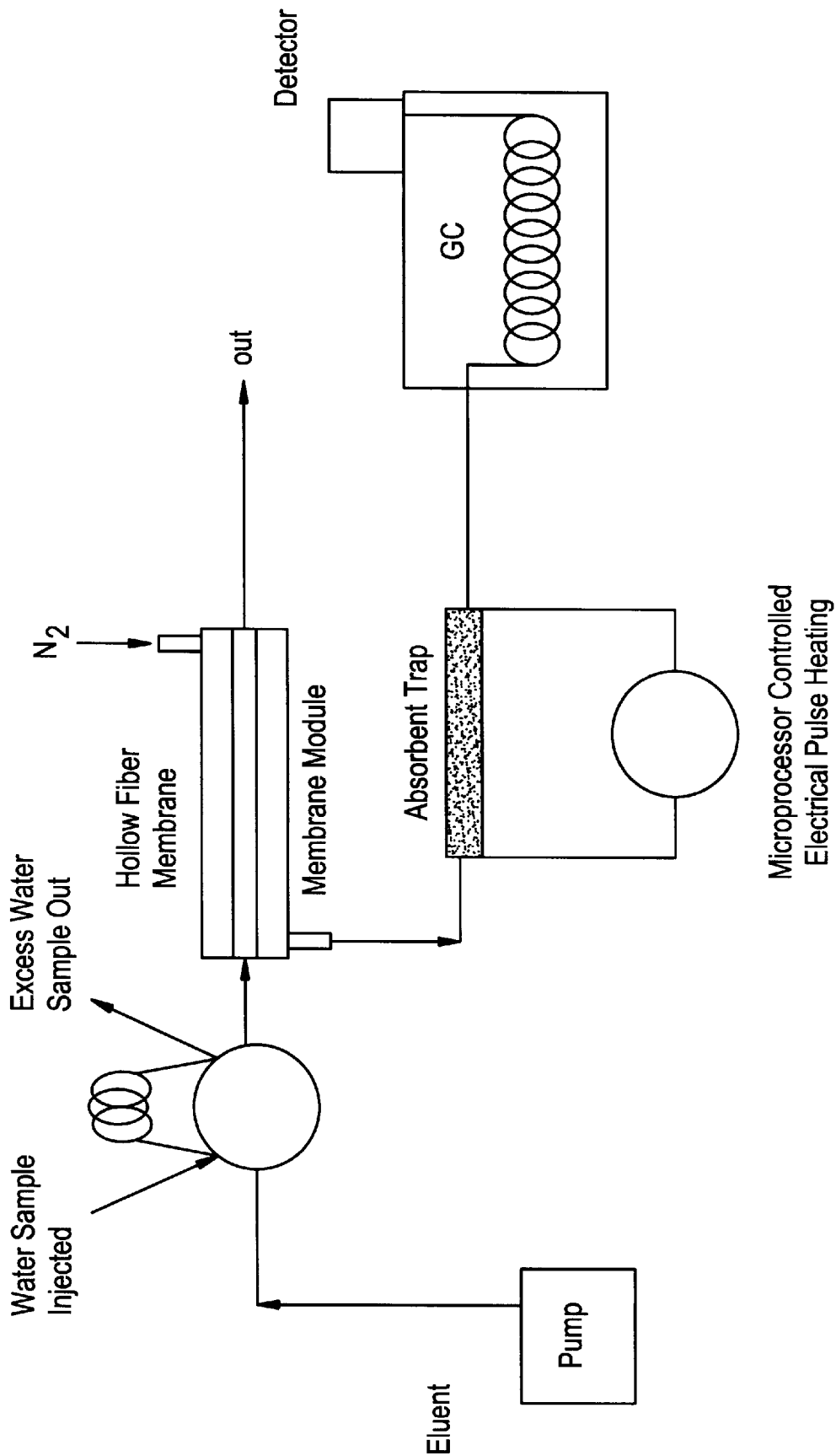
FIG. 16 is a schematic diagram of a water monitoring system.
Figure 17:
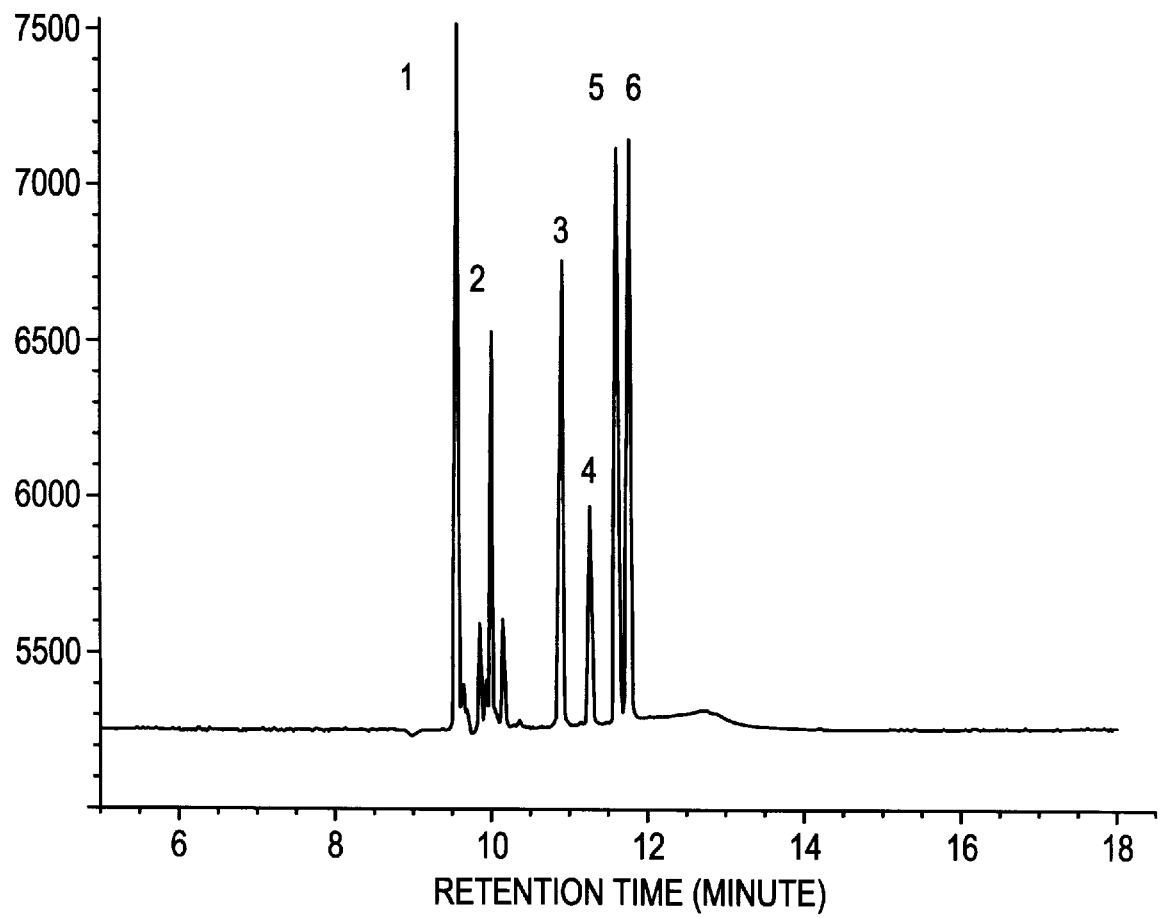
FIG. 17 is a chromatogram generated by injecting a water sample containing ppb levels of organic compound contaminants in the water.

Water Analysis—Where water analysis is being carried out, the organic compound contaminants have to be removed from the water prior to analysis. A membrane may be used for this purpose, as is illustrated in FIG. 16. An eluant fluid, such as pure water, e.g., deionized water, flows continuously through the membrane module which contains one or more hollow fiber membranes. Other designs are also suitable, e.g., one utilizing flat membrane sheets. The water sample containing the organic compound contaminants is injected through an injection valve, e.g., a conventional six-port valve. The eluant fluid carries the sample into the membrane. As the water passes through the membrane, the organic compound contaminants permeate the membrane and are retained in the trap until they are injected into the detector or a GC. It is also possible to simply use an adsorbent trap means connected directly to the GC column, or to use any of the configurations of FIGS. 1–4. In particular, it is possible to use the configuration of FIG. 3 with 2 three-way valves, one on either side of the adsorbent trap, and to carry out the desorption in a backflush mode. This configuration is illustrated in FIG. 4B. The advantages of such backflush desorption have already been described further above. Such backflushing procedures are well known in the art. See, e.g., "Simultaneously Monitor Saturated and Unsaturated C2-C6 Hydrocarbons in Air Samples" *Sample Handling Bulletin* 850A, Supelco Separation Technologies, 1991; and Kebbekus and Mitra, *Environmental Analytical Chemistry*, pp. 8–13, 14, 1996, which are incorporated herein by reference in their entirety. By utilizing these procedures, it is possible to measure the contaminants in a series of water samples retrieved from one or more separate locations. This can be done quickly and efficiently. The adsorbent trap again serves the function of concentrating the organic compound contaminants, separating them from the permanent gases, and injecting them into a gas chromatograph. In this experiment a composite membrane with a silicone coating was used for separating the organic compound contaminants. A variety of other polymer materials can be used, which are non-porous, e.g., silicone-based polymers, or porous, e.g., polypropylene. Composite membranes consisting of a porous core structure having coated thereon a non-porous film, e.g., silicone, can also be used. Single sample analysis is done by making one injection. Continuous analysis can be done by making a series of injections. This system is an alternate to purge and trap analysis. Typical results obtained using this system are shown in FIG. 15. Here a GC is used to separate the different organic compound contaminants from each other. Instead of a GC, other detector means such as TOC/NMOC, MS, FTIR, etc. can also be used.

There are a number of ways in which the analytical apparatus and instrumentation of the present invention differ from those specifically described in U.S. Pat. No. 5,435,169. For example, the methods in the patent focus their attention on chromatographic separation, and rely on a gas chromatograph in most instances. In the present invention, the organic compound contaminants are introduced directly to the detectors without chromatographic separation, but the separation of $CO_2$, $H_2O$ and $CH_4$ from the organic compound contaminants has become a critical part of the present process. In gas chromatography, the injection has to be abrupt, e.g., less than 1 sec, in order to obtain high resolution. In the present process, by contrast, the injection can take place over several seconds. Where water analysis is being carried out, the patent process can only be utilized for continuous monitoring, while the present process can be used either for continuous monitoring, or for analyzing numerous, different samples. The present process also differs in that it relates to determinations of NMOC, direct MS, and direct FID and FTIR detection, which are not emphasized by the processes of the patent.

What is claimed is:

1. A device for the continuous measurement of Non-Methane Organic Carbons (NMOCs) in a fluid sample stream without chromatographic separation, comprising a sampling and concentration system connecting said sample stream to an NMOC detector;

said sampling and concentration system comprising one or more multi-port valves to fluidly connecting said sample stream to an adsorbent trap means;

said adsorbent trap means being capable of rapid heating and cooling, and containing at least one adsorbent composition which adsorbs the NMOCs in said sample stream;

said multi-port valve means fluidly connected to said trap means which allows the venting out of CO, $CO_2$, $O_2$, $N_2$, $SO_2$, $NO_2$, $H_2O$ and other gases in said sample stream so as to concentrate said NMOCs in said trap means;

desorption means associated with said adsorbent trap means whereby said adsorbed NMOCs are rapidly desorbed therefrom and injected into said NMOC detector;

fluid carrier means connecting said sample stream to said adsorbent trap means, and said detector means;

means whereby the one or more multi-port valves operate simultaneously so as to pass said carrier means through the absorbent trap into said detector means so as to carry said desorbed NMOCs from said adsorbent trap means into said detector means as a concentrated pulse.

2. A device according to claim 1 wherein the multi-port valve means comprises a gas sampling valve which makes an injection onto the trap means which retains the NMOC and vents said CO, $CO_2$, $O_2$, $N_2$, $SO_2$, $NO_2$, $H_2O$ and other gases, prior to desorption of the NMOC into said detector.

3. A device according to claim 1 wherein the multi-port valve means comprises two three port valves operating simultaneously with the trap means fluidly connected therebetween.

4. A device according to claim 1 wherein the multi-port valve means passes the sample through the trap means while venting said CO, $CO_2$, $O_2$, $N_2$, $SO_2$, $NO_2$, $H_2O$ and other gases, and further, the valves are switched such that the flow direction of carrier fluid through the trap is reverse of that of the sample to allow backflushing of the trap means during desorption into said detector means.

5. A device according to claim 1 where the process is repeated continuously and repetitively, so as to provide near real-time monitoring of said fluid sample.

6. A device according to claim 1 wherein the said detector means comprises an oxidation means to convert organic to carbon dioxide which is then measured, or further converted to methane using reduction means connected in series with the oxidation means, and measuring the thus-produced methane using FID.

7. A device according to claim 6 wherein the oxidation and reduction means are catalytic and/or thermal.

8. A device according to claim 6 wherein the carbon dioxide is measured by an infrared spectrophotometer.

* * * * *